United States Patent [19]

Jacobs

[11] 4,294,522
[45] Oct. 13, 1981

[54] VISION THERAPEUTIC APPARATUS

[76] Inventor: John T. Jacobs, 1318 Rimrock Dr., San Jose, Calif. 95120

[21] Appl. No.: 934,381

[22] Filed: Aug. 16, 1978

[51] Int. Cl.³ .......................... A61B 3/00; A61H 1/02
[52] U.S. Cl. ...................................... 351/2; 128/25 A
[58] Field of Search ................. 351/2; 128/76.5, 25 A

[56] References Cited

U.S. PATENT DOCUMENTS

| | | | |
|---|---|---|---|
| 2,089,863 | 8/1937 | Updegrave | 351/2 |
| 2,091,173 | 8/1937 | Wottring | 351/2 |
| 2,262,217 | 11/1941 | Wottring | 351/2 X |
| 3,168,894 | 2/1965 | Hollander | 351/2 X |
| 3,277,888 | 10/1966 | Otwell | 128/76.5 |
| 3,664,732 | 5/1972 | Lynn | 351/24 X |
| 3,883,234 | 5/1975 | Lynn et al. | 351/23 |
| 4,105,302 | 8/1978 | Tate | 351/7 |

OTHER PUBLICATIONS

James W. King et al., "Therapeutic Orthoplics," *J. Amer. Optom. Assoc.*, vol. 36, No. 4, pp. 335-344, 4/1965.

*Primary Examiner*—John K. Corbin
*Assistant Examiner*—Rodney B. Bovernick

[57] ABSTRACT

Vision therapeutic apparatus comprising spaced apart displays for showing sequences of images to a viewer-patient. The apparatus provides the capability to vary the rate of image display and keeps score of the occurrence of the special events and the detection or misses thereof by the viewer. In one embodiment, two displays are disposed, generally, in line, one near to and the other distant from the viewer. Each display shows, on a random basis, a series of different images which alternate, image to image, with the series of images shown by the other display. The viewer alternately observes the near and distant displays, thereby performing an optical exercise, and signals to the apparatus when a special visual event occurs, e.g., the successive showing of the same image by the two displays. In another embodiment, two displays are spaced in side by side relation and are simultaneously observable by the viewer. The displays show images at the same time, and a special visual event occurs when the two side by side images, when converged by the eyes of the viewer (this being the optical exercise), form a composite, single image recognizable by the viewer. The spacing of the side by side displays is variable.

6 Claims, 5 Drawing Figures

VISION THERAPEUTIC APPARATUS

TECHNICAL FIELD

This invention relates to therapeutic apparatus for use in the performance of eye exercises for improving reduced or impaired visual capability.

BACKGROUND OF THE INVENTION

It is generally known that functional vision impairments, such as
  a. Myopia (Nearsightedness)
  b. Hyperopia (Farsightedness)
  c. Amblyopia (Lazy Eye)
  d. Presbyopia (Aging Processes or Eye Strain)
  e. Monocular or Binocular Vision Imbalances Muscle and Nerve Imbalance
  f. Learning Disabilities or Poor Vision Perception
  g. Accommodation (Focusing)
  h. Convergence (Centering)
  i. Strabismus (Wandering Eye)
can be corrected or at least improved by the repeated performance of certain eye exercises. For example, amblyopia (lazy eye) can be corrected by having the patient repeatedly alternately focus his lazy eye first on a near and then a distant object while the other eye is patched. To be effective, of course, such exercises must be performed daily. Children, particularly, are often not easily motivated to faithfully perform the exercises and it has not, in the past been generally possible to monitor either the performance of the exercises or the improvements resulting therefrom over short periods of time.

A need exists, therefore, for means for encouraging the faithful performance of various eye exercises, and, as desired, for monitoring the performance of the exercises and the day to day improvements obtained thereby.

SUMMARY OF THE INVENTION

Spaced apart display devices are provided, each of which shows, on a non-predictable basis, a sequence of different images, different ones of the images from one display presenting when matched or merged with different ones of the images of another display, preselected information to the viewer. The viewer monitors the images presented by the displays (the viewer thereby performing the prescribed ocular exercises) and signals to the apparatus when a match or merge is detected. By comparing the signals from the viewer with the actual matches or merges which occur the apparatus provides a record of the level of performance by the viewer.

DETAILED DESCRIPTION

In a first embodiment of the invention, an apparatus (FIG. 1) is provided which can be used in the performance of eye exercises designed to improve or correct poor visual accommodation (focusing). In performing these exercises, the patient repetitively alternately focuses his eyes first on a near object and then on a distant object.

Figure 1:
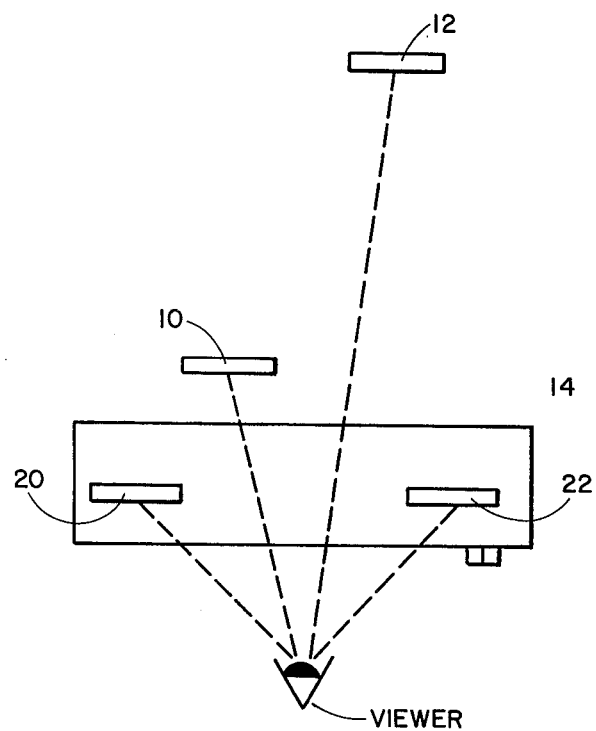
FIG. 1 is a schematic view showing the relationship between apparatus according to this invention and a viewer user of the apparatus.

To this end, the inventive apparatus includes two display devices 10 and 12 for displaying images to be looked at by the patient. Thus, as shown in FIG. 1, the patient is positioned in front of a control box 14 which is wired (not shown) to the two displays, the first display 10 being positioned about 33 to 45 cm away from the patient, or viewer, and the second display 12 being positioned about 6 meters from the viewer.

Any number of different devices can be used for the two displays 10 and 12, e.g., television screens, liquid crystal displays, light emitting diode devices, plasma discharge devices, or the like. In this embodiment, the displays comprise known light emitting diode display cells designed to display individual digits from 0 through 9. But it should be evident that any type of image (e.g. alphanumeric or geometric) could be used. Because of the different distances between the displays and the viewer, the proximal display 10 shows images having dimensions of about 0.18 cm by 0.15 cm while the distal display 12 shows images having dimensions of about 1.0 cm by 0.8 cm. Generally, the distances and sizes are not critical.

As previously described, a visual exercise performed with this apparatus involves having the viewer alternately focus on different displays. To this end, in this embodiment, the two displays show images on an alternating, non-overlapping time basis, one display turning on immediately after the other turns off. The on time of the two displays is the same, although the on time of the displays can be varied, under the control of the viewer to change the condition of the exercise.

To provide interaction between the viewer and the apparatus, a "special" visual event is caused to occur on a non-periodic basis which must be detected by the viewer. This special event, in this embodiment of the invention, is the display of successive images which convey a predetermined informational message to the viewer. For example, using digits as the displayed images, the special event is the showing by one display of some digit (any) and the successive showing by the other display of the same digit.

At other, "non-special" times, the successive images shown by the two displays are different.

In use of the apparatus, an object is for the viewer to detect the occurrence of the special event, i.e., in this embodiment, the repetition or matching of the same digits in successive displays. This requires the alternate focusing of the eyes of the viewer on the successive images as they are alternately displayed by the near and distant displays. Such alternate focusing, of course, is the desired ocular exercise. Matching as used herein refers to the correspondence of two (or more) images which are suitably associated with each other.

In order to avoid "cheating" by the viewer, i.e., anticipation of the occurrence of a matching of images, such occurrences are made to happen on a random, non-predictable basis.

In this embodiment, each display is capable of displaying 10 different images (digits), and, on a purely random basis, the probability of a match occurring is only 1 to 100. This may result in an excessively long time between the occurrence of matches, leading to possible loss of interest by the viewer. To avoid this, the waiting time, or the maximum period between matches, is arbitrarily reduced. One way, of course, is by simply reducing the number of different images which can be displayed. Alternately, the preferably, means are provided, described hereinafter, whereby after a certain number of mismatches, such number being selected on a random basis, a match is forced. That is, after the randomly selected number of mismatches occurs, such number not being in excess of some relatively low number, e.g., four, the particular image then being shown on one display is noted by the apparatus, and that same image is then made to appear on the other display immediately thereafter.

When such a match occurs, the viewer, if he detects it, signals such detection to the apparatus, as by depressing a button on the control box 14. A score of the viewer's performance is preferably kept by the apparatus: correct detections adding to the score.

Additionally, the rate of accommodation or the rate at which the images alternate between the near and distal display is variable and under patient control. By varying the rate of accommodation, and judging percentage of correct response, the performance level of an individual can be determined.

To sustain the attention of the viewer, immediate feedback of his performance is preferably provided. For example, if a match is missed, the alternating sequence of images is interrupted, and both images are displayed simultaneously and caused to rapidly turn on and off in a series of "blinks". When a match is properly detected, an audible signal, such as a bell, can be sounded. Other indications of performance are, of course, possible. In this embodiment two displays are used; but it should be evident that more than two displays positioned at different lengths and different spatial angles from the viewer could be used with due care for size of display and viewing angle.

In a second embodiment of the invention, apparatus is provided which is used in connection with eye exercises designed to correct for convergence insufficiency.

These exercises consist of having the patient cross (center) his eyes while observing two adjacent images to generate a third image centered therebetween which is a composite or blending of the two individual images.

To this end, in accordance with this invention, two movably mounted displays 20 and 22 (FIG. 1) are provided, conveniently on the control box 14 itself, in side by side relation to each other. In this embodiment, the apparatus is designed to be used with a viewer positioned so that his eyes are spaced about 40 cm from the displays 20 and 22. Each display 20, 22, shows images having dimensions of about 1.0 cm by 0.8 cm. The images shown are spaced apart (center to center) a distance which may be varied by a mechanism (not shown) from between 2 cm and 10 cm.

Figure 2A:
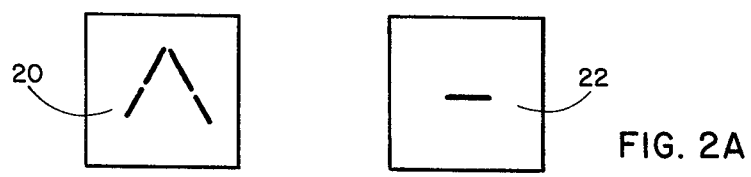
FIGS. 2A and 2B illustrate images displayed by two displays in accordance with one embodiment of the invention.
Figure 2B:
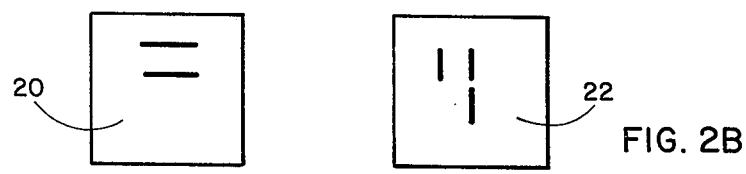

As in the first embodiment herein described, each display shows a sequence of various images on a non-predictable basis. In this embodiment, the two images are shown simultaneously, and, in general, the various images shown by one display are different from the images shown by the other display. Also, the various individual images shown are not composite images in themselves, i.e., they convey no intelligence, or only partial intelligence, to the viewer on an individual basis, but different ones of the images from one display form part of a composite image recognizable by the viewer when viewed with certain ones only of the other display. For example, the left hand display 20 is programmed to show only certain segments or portion of various digits, such as (FIG. 2B) part of the digit 9.

Conversely, the right hand display 22 is programmed to show only the remaining segments or remainder of the portions of the digits. The visual "Special event" or matching occurs when the segments of the right and left hand displays optically combine to form a valid image (as in FIGS. 2A and 2B which show a matching of the portions forming letter "A" and the digit 9). Because, however, the two digit portions are displayed in spaced apart relation and, preferably, for only a short duration, e.g., 0.7 to 2 seconds, recognition of the matched parts requires that the viewer's eyes correctly perform the convergence function. Here also any other type of images (e.g., alphanumeric, geometric, . . . ) could be used to form the displays.

As in the first embodiment herein described, the viewer interacts with the apparatus by signaling to it when a match is detected. The apparatus keeps score of the viewer's performance and also provides instantaneous feedback to the viewer concerning his performance. For example, if a correct merge is missed by the viewer, some signal to that effect is provided by the apparatus. On the other hand, if a "proper" merge is correctly identified then a corresponding indication is provided by the apparatus.

The block diagram of an electronic system for enabling the performance and control of the eye exercises described above is shown in FIG. 3. Major components of the system are described below:

1. The system includes a viewer controlled (momentary) switch S1 which when set (actuated) to position 1 applies a signal defined as a logic "1" or "1" to the system. The actuation of switch S1 initiates all new exercise cycles. Subsequent to the initiation of an exercise (merge/match) cycle the viewer actuates switch S1 to indicate the recognition of a match or merge of the images displayed. The output of switch S1 or a signal derived from the closure of switch S1 is applied to three random number generators RNG1, RNG2 and RNG3, and to various registers used in monitoring and controlling the eye exercises.

2. The random number generators RNG1, RNG2, and RNG3 generate signals for activating the segments of the displays which are, by way of example, seven (7) segment LED digital displays. Each one of the random number generators includes a gated oscillator connected to a counter. In an operating unit embodying the invention free running multivibrators were used to make the oscillators and their frequency of oscillation were determined by separate RC networks. The oscillator frequencies are subject to random variations (due to internal jitter and noise) which is sufficient to produce a random count in the three decade counters. The oscillators and counters could be any one of a number of known circuits and need not be further detailed. The random numbers RN1, RN2 and RN3 generated by Random Number Generators RGN1, RGN2, RGN3 are in a binary coded decimal (BCD) format. The output of RNG1 is coupled to the input of a Decoder/Driver 1 whose output is coupled to the Proximal display 10 and the output of RNG2 is coupled to the distal display 12. The decoder/drivers convert the BCD information into suitable signals to drive the seven segment displays. (Although, in the drawing, a single line is shown interconnecting one or more block or component to another, the line may include more than one wire or connection.)

3. The system also comprises a system timing generator 31 which includes circuitry for determining:
   a. the sequence in which the displays are activated,
   b. the length of time the displays are energized,
   c. the score; and
   d. the generation of new numbers for succeeding cycles after the first.

Signals from the timing generator coupled to decoder/drivers 1 and 2 control the sequence in which the displays are activated and the length of time each display is energized. The timing generator also includes circuitry for generating multi-(4)-phase signals ($\phi_1$, $\phi_2$, $\phi_3$ and $\phi_4$) which produce 4 distinct time slots per cycle during which different control and display functions are performed. The system timing generator is on or triggered when S1 is closed at the start of a new cycle and the four-phase signals are then generated.

4. The system also includes
   a. a Trial Register (TR) 33 for counting the number of times the viewer was tested and a comparator 35 for comparing the output X of TR 33 and the output RN3 of RNG3. A function of comparator 35 is to generate a signal which will force a match between RN1 and RN2 if no match has occurred between RN1 and RN2 for a predetermined number of trials (e.g., 4)
   b. an Attempt Register (AR) 37 for counting the number of times the viewer has detected or should have detected a match, and a comparator 39 for comparing the output Y or AR 37 and a fixed number N (e.g. 10) of tries which is arbitrarily set as the number of trials per exercise cycle;
   c. a score register 41 which is incremented each time a correct answer is made by the viewer and whose contents are displayed on display 8 located on control box 14 at the end of each complete set or exercise cycle.

A Match exercise is now briefly described. A "Match" exercise is initiated by actuating or depressing switch S1. Then, under control of signal $\phi_1$, during a time T1, the random number RN1 produced by RNG1 is displayed by proximal display 10. Subsequently, under control of signal $\phi_2$, during a time T2, the random number RN2 produced by RNG2 is displayed by distal display 12. During time T2 the score monitoring period occurs. If the viewer detects a match between the displayed images he must depress S1 during the T2 time interval. Time intervals T1 and T2 are generally of similar duration and may be much longer than time intervals T3 and T4. Under the control of signal $\phi_3$, during a time T3 subsequent to T2, the scoring is tabulated. Four possible conditions to be tabulated exist.
   a. If RN1 is equal to RN2 and viewer has set (during T2) S1=1, a correct answer is indicated by a clearly recognizable audio signal. The score register (SR) 41 and attempt register (AR) 37 are incremented by one (1). The count in attempt register 37 is compared to the number ten (10) (10 having been arbitrarily selected as the number of matches to be displayed per each set of exercise cycle). If the output of AR 37 is equal to 10 then the score stored in SR 41 is displayed on display 8 mounted on control box 14. If the output of AR 37 is not equal to 10, switch S1 must again be depressed to initiate a new display.
   b. If RN1$\neq$RN2 and S1 had been set to 1, a wrong answer is indicated. The AR 37 is incremented and a signal is generated and supplied to the displays causing the blinking of the displays. The count in AR 37 is again compared to 10, with the score displayed if the count is equal to 10 and with the requirement for S1 to be depressed if the count is less than 10.
   c. If RN1 is equal to RN2 and S1 is set to 0 (i.e., had not been depressed during T2) a wrong answer is indicated and the sequence identified in paragraph 2, directly above, is repeated.
   d. If RN1 is not equal to RN2 and S1 is equal to zero an invalid or no match condition is indicated, the numbers generated by RNG1 and RNG2 keep cycling until a match occurs or a match is forced by RNG3 as described below. The Trial Register (TR) 33 is incremented and its output (Z) is compared with the number RN3, at the output of RNG3. If X is equal to RN3, a signal is generated and coupled to RNG1 and RNG2 forcing them to the same number on the next try or trial. (Note, RN1 will equal RN2, but the value of the number is not predetermined.) Following the tabulation period T3, a signal $\phi_4$ is generated setting up a period T4 during which new random numbers are generated. If at the end of a cycle, the output of AR 37 is equal to 10 the exercise is completed and the contents (number of correct attempts out of 10) of the score register 41 are displayed on display 8.

The Merge exercise is essentially the same as Match insofar as the timing, scoring and number generation are concerned. The major difference is that the two merge digits, placed side by side a variable distance apart, contain random combinations of segments, which may or may not form a valid digit. During $\phi_1$, the decimal points on the left hand and right hand displays are shown enabling the player to concentrate on merging them together. During $\phi_2$, the random segments are displayed and if the two displays merge to form a valid number and S1 equals 1, a right answer is obtained. The rate of display is variable and under viewer control. (Scoring and timing are otherwise as described for MATCH). Choice and orientation of the activated display segments for the left and right had displays are determined by the random numbers RN1 and RN2 and the merge gating logic block 43 shown in FIG. 3B.

Figure 3A:
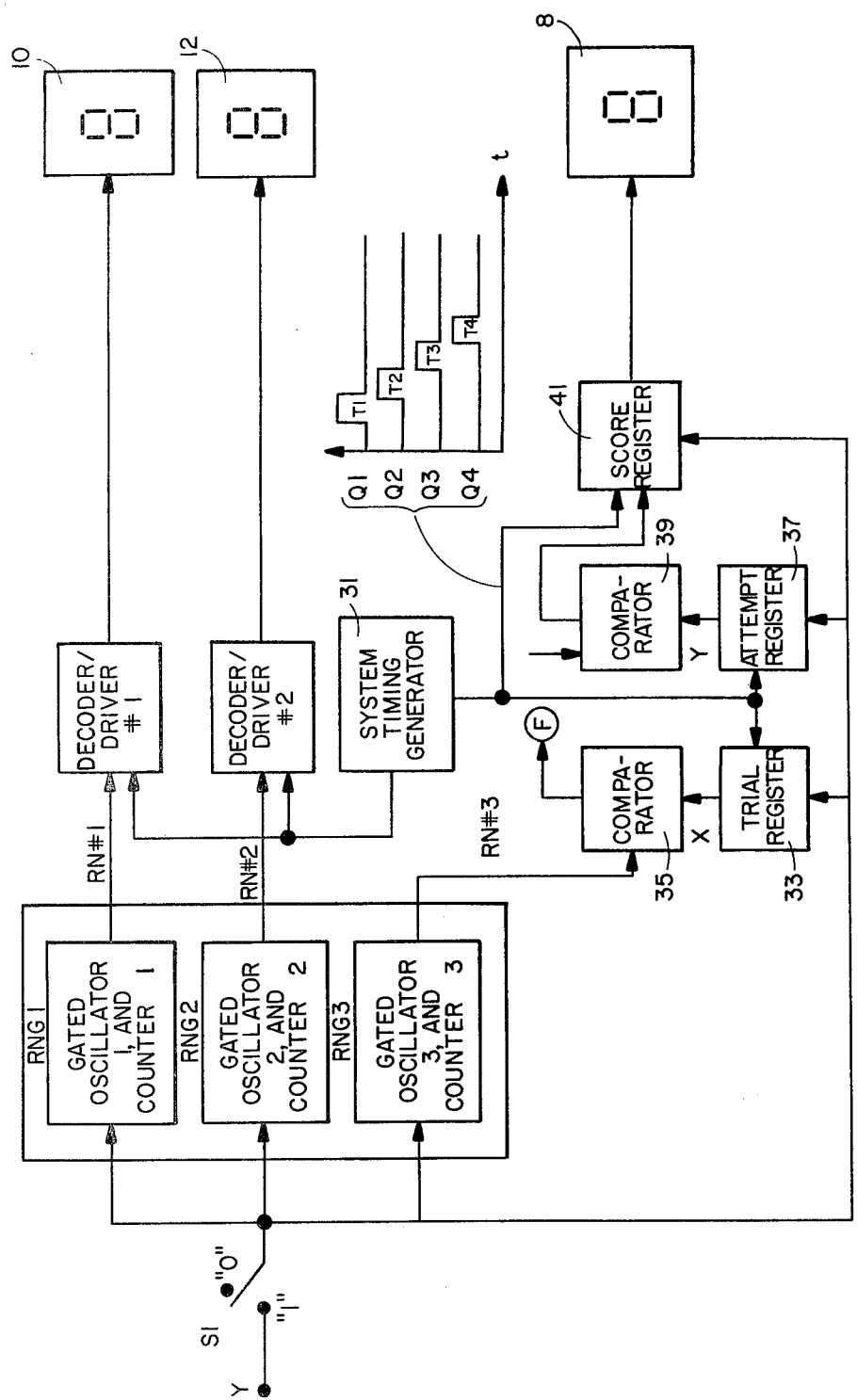
FIGS. 3A and 3B are block diagrams of the electrical system of an embodiment of the inventive apparatus.
Figure 3B:
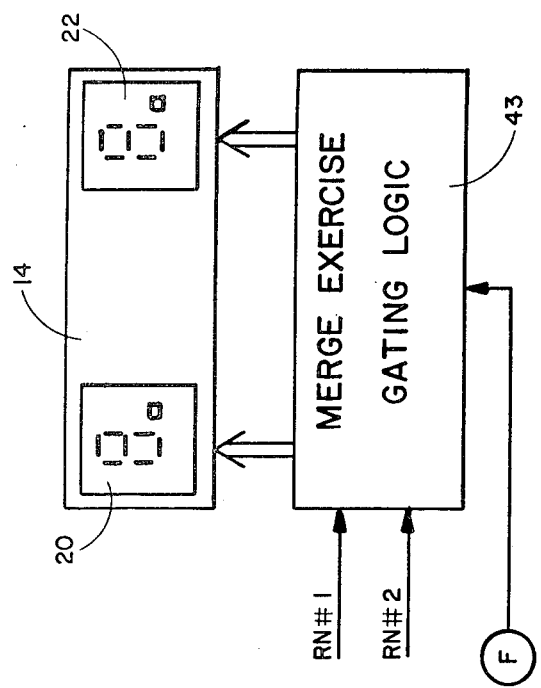

It should be appreciated that an electronic system of the type shown and illustrated in FIGS. 3A and 3B or one performing a similar function could be connected to standard television receivers for performing the convergence or merge exercises.

It should also be appreciated that the displays can be made with different colors or be provided with filters so as to appear to be of different colors. Likewise the viewer-patient can be made to wear a pair of glasses on which are mounted filters whereby only if he uses both eyes correctly as intended by the exercise will the viewer be able to converge or match the images.

It should also be appreciated that the match exercise can be implemented in a great number of variations which can improve not only visual acuity but also mental acuity. For example, one version of the exercise could be implemented by assigning a target image initially to the patient and requiring that he retain that image in his memory and match that retained image on either the near or distal display as the random images are alternately displayed. This exercise would improve both visual and mental acuity.

It should also be appreciated that more than two displays could implement the match exercise and the random symbol would be randomly displayed across the set of spatially distributed displays. The patient would then have to determine which display contains the image during each cyle of the exercise and also match the contents of that display with the target symbol.

What is claimed is:

1. Vision thereapeutic apparatus comprising means for automtically generating sequences of different images at different spaced apart locations, different ones of the images displayed at one of the locations providing preselected information when matched with preselected ones of the images displayed at another of said locations, the images at each of said locations being selected for display on a non-predictable basis among various other images not providing said preselected information, whereby said matching occurs on a non-predictable basis, and means for detecting responses from the user indicative of his observations of said images.

2. Apparatus in accordance with claim 1 wherein said locations are spaced apart in a direction away from the user.

3. Apparatus in accordance with claim 1 including means, operative upon the failure of the generation of matching pairs of said images after the generation of a non-predictable number of successive images not exceeding a preselected number, for automatically causing the generation of a matching pair of said images.

4. Apparatus in accordance with claim 1 wherein said different spaced apart locations are multiple locations which are spaced apart in a direction away from the user, and wherein the images displayed at said multiple locations alternate in time with one another, whereby the user is required to focus his eyes on each of the locations on an alternating, repetitive basis, a matching of images occurring when an image appearing at one of said locations provides said preselected information with the immediately following image appearing at the other of said locations.

5. Apparatus in accordance with claim 1 wherein said locations are in side by side relation and simultaneously observable by, the user, and wherein images are presented simultaneously at the locations, a matching of images occurring when each of the images then being displayed forms a different part of a composite image recognizable by the user, such recognition requiring the performance of an eye convergence exercise by the user.

6. Apparatus in accordance with claim 1 including means for selecting different rates at which said sequences of images are generated.

* * * * *